United States Patent [19]

Shinozuka

[11] Patent Number: 4,633,871
[45] Date of Patent: Jan. 6, 1987

[54] BASKET FORCEPS ASSEMBLY
[75] Inventor: Minoru Shinozuka, Hachioji, Japan
[73] Assignee: Olympus Optical Company, Ltd., Japan
[21] Appl. No.: 728,783
[22] Filed: Apr. 30, 1985
[30] Foreign Application Priority Data
 Jun. 18, 1984 [JP] Japan ................. 59-124630
[51] Int. Cl.⁴ .................................. A61B 17/28
[52] U.S. Cl. ............................ 128/321; 128/319
[58] Field of Search ............ 128/321, 322, 323, 324, 128/319; 294/99 R, 99 S, 100

[56] References Cited
U.S. PATENT DOCUMENTS
2,670,519  2/1954  Recklitis .................. 128/321
4,094,131  6/1978  McElvey .................. 119/106
4,467,802  8/1984  Maslanka ................. 128/321
4,483,562  11/1984  Schoolman ............... 128/321

FOREIGN PATENT DOCUMENTS
2316187  11/1983  Fed. Rep. of Germany .
57-78843  5/1982  Japan .

Primary Examiner—Gene Mancene
Assistant Examiner—David I. Tarnoff
Attorney, Agent, or Firm—Ostrolenk, Faber, Gerb & Soffen

[57] ABSTRACT

A basket forceps assembly which includes a plurality or resilient wires which are biased to define a basket. Two types of resilient wires are used which exhibit different tensile strengths.

10 Claims, 7 Drawing Figures

U.S. Patent  Jan. 6, 1987  4,633,871
FIG. 1
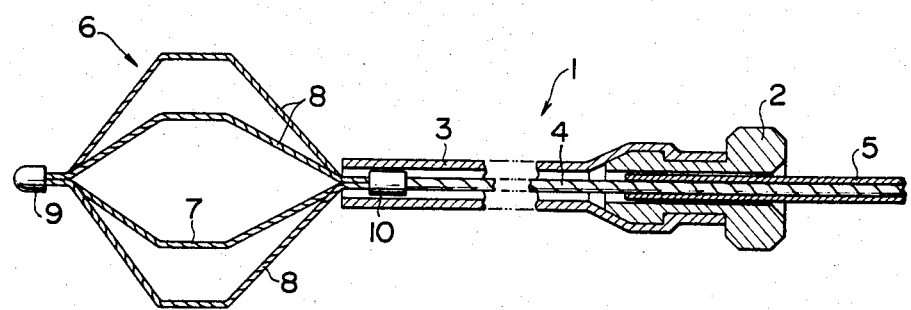
FIG. 2  FIG. 3
FIG. 4
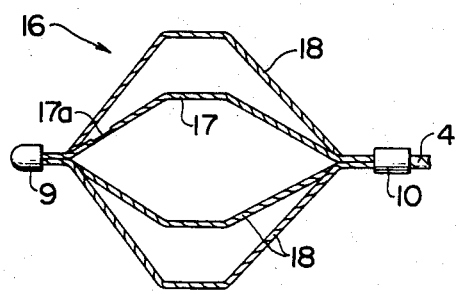
FIG. 5
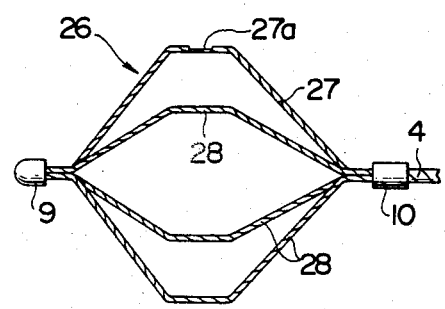
FIG. 6  FIG. 7
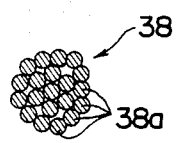 

BASKET FORCEPS ASSEMBLY

BACKGROUND OF THE INVENTION

The invention relates to a basket forceps assembly, and more particularly, to a basket forceps assembly formed by a plurality of resilient wires. Said assembly is capable of receiving and holding foreign matter, such as biliary calculus, situated within a coelom and is capable of removing the foreign matter from the coelom.

The removal of foreign matter, such as biliary calculus, from the coelom can be accomplished by using an endoscope. Removal generally takes place by grasping the calculus located within the bile ducts by means of a basket and by carrying it through a teat to the duodenum. Where the size of the biliary calculus is greater than a restricted area within the teat and such size renders the extraction difficult, the biliary calculus is temporarily left at the restricted area, and a separate picking means is used to remove it from the coelom.

A basket forceps assembly is used as a recovery means extract foreign matter, such as biliary calculus, from the coelom. As is well recognized, such basket forceps assembly comprises a flexible tube which is received within and passes through a forceps receiving channel formed in an endoscope, and a basket which is capable of grasping a foreign matter, the basket being defined by a plurality of resilient wires which are disposed in a distal end of the flexible tube so as to be movable out of and into the latter. An operating wire extends through the flexible tube, and when operated, causes the basket to project forward of the distal end of the flexible tube. The wires are biased for displacement upon projection out of the distal end, thereby forming a basket.

The resilient wires which are used to define the basket generally comprise strands, each of which comprises a plurality of resilient filaments which are twisted together. Since each of the plurality of resilient wires includes the same number of filaments which are of an equal diameter and of a same material, these wires all exhibit a similar tensile strength.

Accordingly, when the basket is used to grasp a foreign matter, such as biliary calculus, and when the operating wire is towed to a greater degree imposing an increased stress upon each of the resilient wires, they may be broken all at the same time. It will be seen that when broken, the resilient wires are left within the coelom, and must be removed by conducting a surgical operation, thus causing undesirable pains to a patient.

SUMMARY OF THE INVENTION

It is an object of the invention to provide a basket forceps assembly having increased safety and which eliminates the described disadvantage of the prior art.

In accordance with the invention, a plurality of resilient wires which are used to define a basket are formed by at least two types of wires having different tensile strengths. This eliminates the simultaneous breakage of all the resilient wires. In the event the breakage of a wire or wires occurs, only those wires having reduced tensile strength will be broken, thus avoiding the occurrence of a situation that the resilient wires which form the basket may be left within the coelom. In this manner, a basket forceps assembly having increased safety is provided.

BRIEF DESCRIPTION OF THE DRAWINGS

FIG. 1 is a longitudinal section of a basket forceps assembly according to one embodiment of the invention;

FIGS. 2 and 3 are enlarged cross sections of resilient wires having different tensile strengths;

FIG. 4 is a side elevation of a basket assembly including a resilient wire of a reduced tensile strength;

FIG. 5 is a side elevation of a modification of the basket shown in FIG. 4; and

FIGS. 6 and 7 are enlarged cross sections of resilient wires having different tensile strengths.

DESCRIPTION OF PREFERRED EMBODIMENTS

Referring to FIG. 1, there is shown a basket forceps assembly 1 comprising a flexible tube 3 of a diameter which permits it to be passed through a forceps receiving channel, not shown, defined within an endoscope, said flexible tube having a fitting 2 attached thereto at its proximal end, and a basket 6 formed by a plurality of resilient wires which are received within a distal end of the flexible tube 3. The basket 6 is movable out of and into the distal end of the flexible tube 3 when an associated operating wire 4 is operated. The operating wire 4 extends through the flexible tube 3. The operating wire has a distal end to which a proximal end of the basket 6 is secured and a proximal end which extends through the fitting 2 and which is surrounded by an operating tube 5 which is disposed to extend out of the fitting 2 located on the proximal end of the flexible tube 3.

The basket 6 may comprise four resilient wires, for example. These four resilient wires are previously biased in a manner such that their central portions are resiliently displaced in a direction perpendicular to the direction of projection in an expanding manner whenever they project forwardly from the distal end of the flexible tube 3. As mentioned previously, each of the resilient wires comprises a plurality of resilient filaments which are twisted together to prevent them from being loosely disassembled. Of these four wires, one indicated at 7 is formed to exhibit a reduced tensile strength as compared with the tensile strength of the remaining three wires 8.

Specifically, referring to FIGS. 2 and 3, the wire 7 comprises a reduced number of filaments as compared with the number of filaments which form the resilient wire 8, resulting in a reduced tensile strength. The front ends and the rear ends of these resilient wires 7, 8 are bundled together by a front end tip 9 and a rear end tip 10, respectively. It will be noted that the rear end tip 10 is secured to the distal end of the operating wire 4.

In operation, the operating tube 5 is initially pulled toward a user in order to retract the resilient wires 7, 8, which form the basket 6, into the distal end of the flexible tube 3. As they retract, the inner wall of the flexible tube 3 at its distal end causes the basket 6 to shrink so as to be contained within the distal end of the flexible tube.

The flexible tube 3 under this condition is passed into a forceps receiving channel defined within an endoscope that is previously inserted into coelom, thus introducing the basket forceps assembly 1 into the interior of a physical body. If foreign matter, such as biliary calculus, is then found within the bile ducts, it may be extracted by driving the operating tube 5 inward to cause the individual resilient wires 7, 8 to project out of the distal end of the flexible tube 3. Thereupon, the wires 7, 8 expand the bile ducts and also expand themselves to form the basket 6, allowing the foreign matter to be received therein through spaces between adjacent wires 7, 8. Subsequently, the operating tube 5 may be pulled toward a user to reduce the size of the basket 6, whereby the foreign matter is retained within the basket 6. The foreign matter can then be extracted from the coelom through the teat and the duodenum when the endoscope is removed from the physical body.

In the event the operating tube 5 is pulled too strongly or too rapidly, the wire 7 having a reduced tensile strength compared with the tensile strength of the remaining wires may be broken while the other wires 8 do not break. As a result, the foreign matter which is once grasped may be released from within the basket 6, but the elements which constitute the basket 6 can be extracted from the coelom without being left therein.

FIGS. 4 and 5 show modifications of the basket forceps assembly according to the invention. A basket 16 shown in FIG. 4 differs from the embodiment shown in FIG. 1 in that the construction of a resilient wire having a reduced tensile strength is changed. Specifically, one, shown at 17, of four resilient wires which form the basket 16 has part 17a wherein part of its constituent filaments are removed at a location toward the front end of the basket, and thus said resilient wire 17 exhibits a tensile strength which is reduced as compared with the tensile strength of the three remaining resilient wires 18. In a basket 26 shown in FIG. 5, one, shown at 27, of four resilient wires which form the basket 26 has part of its filaments 27a removed at a central location thereof, and thus said resilient wires 27 exhibits a tensile strength which is reduced as compared with the tensile strength of the three remaining resilient wires 28. In other respects, the arrangement is similar to the basket 6 shown in FIG. 1.

The baskets 16, 26 constructed in these manners operate in the same manner, and achieve a similar effect as, the embodiment shown in FIG. 1 since an increased stress applied to these baskets causes the selected wire 17 or 27 having a reduced tensile strength to be broken at a portion 17a or 27a thereof. The location where part of the filaments is removed to produce a reduced tensile strength may be shifted toward the rear end of the basket in the modifications shown in FIGS. 4 and 5.

FIGS. 6 and 7 illustrate further modifications. Specifically, in FIG. 6, a resilient wire 38 comprises a plurality of resilient filaments 38a which are twisted together in the same manner as mentioned before, but which are formed of a material different from the material which is used to define the remaining resilient wires of the basket. The material chosen for the resilient wire 38 may be one which has a lower fracture strength than the material used to form the remaining wires. In FIG. 7, a resilient wire 48 which has a reduced tensile strength is formed of filaments 48a having a reduced diameter than the diameter of filaments which are used to form the remaining resilient wires of the basket. Again, an increased stress applied to these resilient wires causes the selected resilient wire 38 or 48 which has a reduced tensile strength to fracture initially, thus achieving the object of the invention.

As an alternative, more than one resilient wire may be constructed to exhibit a reduced tensile strength, or the tensile strength may vary from wire to wire.

What is claimed is:

1. A basket forceps assembly for use with an endoscope comprising:
    a flexible tube having a distal end which can be passed through a forceps receiving channel of an endoscope;
    a plurality of resilient wires which are received in the distal end of said flexible tube so as to be movable out of and into the distal end and said resilient wires being bundled together at each of their ends and further being biased so as to define a basket to grasp foreign matter therein when said resilient wires project out of the distal end of said flexible tube;
    a human actuable operating means connected to said resilient wires so as to enable an operator to move said resilient wires into and out of the distal end of said flexible tube; and
    said resilient wires further characterized in that at least one of the resilient wires have tensile strengths which are lower than different, higher tensile strengths, associated with remaining ones of said plurality of resilient wires so that if any one of said at least one wires break all of said plurality of wires remain connected to said basket and are retrievable from the location of said foreign matter.

2. A basket forceps assembly according to claim 1 in which each of the resilient wires comprises a plurality of filaments which are twisted together, and in which one of the wires includes a reduced number of filaments as compared with another of the remaining wires.

3. A basket forceps assembly according to claim 1 in which each of the resilient wires comprises a plurality of filaments which are twisted together, and wherein one of the resilient wires of the plurality has part of its filaments removed at a predetermined location along that wire, thus reducing the tensile strength of the wire.

4. A basket forceps assembly according to claim 1 in which one of the resilient wires of the plurality is formed by a material having a tensile strength which is less than the tensile strength of a material used to form another of the remaining resilient wires.

5. A basket forceps assembly according to claim 1 in which each of the resilient wires comprises a plurality of filaments which are twisted together and in which one of the resilient wires is formed by filaments having a diameter which is less than the diameter of filaments used to define another of the remaining resilient wires.

6. A basket to grasp foreign matter for use with a basket forceps assembly comprising:
    a plurality of resilient wires being bundled together at each of their ends and being biased so as to define a basket to grasp foreign matter therein when said plurality of resilient wires is in an expanded position; said plurality of resilient wires capable of being passed through a flexible tube of a basket forceps assembly when said plurality of resilient wires is in an unexpanded position; and
    said resilient wires further characterized in that at least one of the resilient wires have tensile strengths which are lower than different, higher tensile strengths, associated with remaining ones of said plurality of resilient wires so that if any one of said at least one wires break all of said plurality of wires remain connected to said basket and are retrievable from the location of said foreign matter.

7. A basket forceps assembly according to claim 6 in which each of the resilient wires comprises a plurality of filaments which are twisted together, and in which one of the wires includes a reduced number of filaments as compared with another of the remaining wires.

8. A basket forceps assembly according to claim 6 in which each of the resilient wires comprises a plurality of filaments which are twisted together, and wherein one of the resilient wires of the plurality has part of its filaments removed at a predetermined location along that wire, thus reducing the tensile strength of the wire.

9. A basket forceps assembly according to claim 6 in which one of the resilient wires of the plurality is formed of a material having a tensile strength which is less than the tensile strength of a material used to form another of the remaining resilient wires.

10. A basket forceps assembly according to claim 6 in which each of the resilient wires comprises a plurality of filaments which are twisted together and in which one of the resilient wires is formed by filaments having a diameter which is less than the diameter of filaments used to define another of the remaining resilient wires.

* * * * *